(12) United States Patent
Besko

(10) Patent No.: US 9,302,089 B2
(45) Date of Patent: Apr. 5, 2016

(54) CONNECTORS WITH ELECTRICAL ELEMENTS

(71) Applicant: ORIDION MEDICAL 1987 LTD., Jerusalem (IL)

(72) Inventor: David P. Besko, Thornton, CO (US)

(73) Assignee: Oridion Medical 1987 Ltd., Jerusalem (IL)

( * ) Notice: Subject to any disclaimer, the term of this patent is extended or adjusted under 35 U.S.C. 154(b) by 241 days.

(21) Appl. No.: 14/259,397

(22) Filed: Apr. 23, 2014

(65) Prior Publication Data

US 2015/0306365 A1    Oct. 29, 2015

(51) Int. Cl.
| | | |
|---|---|---|
| *A61F 5/44* | (2006.01) | |
| *A61M 39/10* | (2006.01) | |
| *G11C 16/02* | (2006.01) | |
| *H01R 9/11* | (2006.01) | |
| *H01R 13/66* | (2006.01) | |

(52) U.S. Cl.
CPC ............ *A61M 39/10* (2013.01); *A61M 39/1011* (2013.01); *G11C 16/02* (2013.01); *H01R 9/11* (2013.01); *H01R 13/6616* (2013.01); *A61M 2039/1005* (2013.01); *A61M 2039/1022* (2013.01); *A61M 2039/1044* (2013.01); *A61M 2205/43* (2013.01); *A61M 2205/52* (2013.01); *A61M 2205/6018* (2013.01); *A61M 2205/6027* (2013.01)

(58) Field of Classification Search
CPC ........................... A61M 25/01; A61B 17/0057
USPC .................................. 604/264, 328, 327, 317
See application file for complete search history.

(56) References Cited

U.S. PATENT DOCUMENTS

| | | | |
|---|---|---|---|
| 3,452,366 A | | 7/1969 | Downey |
| 6,663,437 B2 * | | 12/2003 | Korsunsky ......... H01R 13/6658 439/620.06 |
| 6,987,659 B1 * | | 1/2006 | Epstein ................ H05K 9/0066 361/212 |
| 7,088,054 B2 * | | 8/2006 | Erlbacher .............. H05B 41/30 315/200 A |
| 2003/0087558 A1 * | | 5/2003 | Korsunsky ......... H01R 13/6658 439/676 |

FOREIGN PATENT DOCUMENTS

| | | |
|---|---|---|
| DE | 102011088505 | 6/2013 |
| GB | 2466099 | 6/2010 |
| WO | 2008137813 | 11/2008 |
| WO | 2010087764 | 8/2010 |

* cited by examiner

*Primary Examiner* — Phuongchi T Nguyen
(74) *Attorney, Agent, or Firm* — Rodney J. Fuller; Booth Udall Fuller, PLC

(57) ABSTRACT

Tube connector including two conductive elements and a resistor and/or capacitor electrically connected therebetween, the two elements arranged such that an electrical circuit including the two conductive elements and the resistor and/or capacitor will be closed when the tube connector mates with a device connector of a medical device.

14 Claims, 9 Drawing Sheets

CONNECTORS WITH ELECTRICAL ELEMENTS

TECHNICAL FIELD

The present disclosure relates generally to the field of connectors for connecting a tube or a cable to a medical instrument.

BACKGROUND

Medical instruments often need to be temporarily connected to analyzing devices, such as medical devices, via connectors. Such connectors are used as mediators for connecting between the medical device interface (the instruments itself) and constituents, such as tubes, cannulas, pulse oximeter probes, Electrocardiography (ECG) or Electroencephalography (EEG) electrodes, non-invasive blood pressure (NIBP) Cuffs and other elements.

SUMMARY

The present disclosure relates to tube connectors including conducting bands and a resistor placed across the bands and arranged such that an electrical circuit including the conductive elements and the resistor will be closed when the tube connector mates with a device connector of a medical device.

The present disclosure also relates to tube connectors including conducting bands and a capacitor placed across the bands and arranged such that an electrical circuit including the conductive elements and the capacitor will be closed when the tube connector mates with a device connector of a medical device.

The connectors of the present disclosure may for example be used in a respiratory gas sampling and/or delivery tubing systems. Such connectors are typically located at a distal end of a sampling line and are configured to connect a sampling tube to a fluid analyzer, such as a gas analyzer, for example a capnograph.

The connectors of the present disclosure include at least one resistor and/or capacitor which enables identification of the connectors. Accurate identification of the connector may be of uttermost importance for ensuring correct connection between a medical device and its constituents such as tubes, probes etc. The constituents are often of the disposable type, are frequently replaced and may require abrupt connection for example in emergency situations. To avoid sometimes fatal misconnections as well as optimal functioning of the instrument, it can be necessary to ensure that the medical device is only activated when a correct tube is properly connected and authenticated.

The connectors of the present disclosure may be configured to ensure that a medical device be activated only when a correct connector is properly connected. Similarly, the connector may be configured to ensure that a medical device is deactivated when the connector is withdrawn. This may prevent operation of a medical device when no constituent is connected or even when a correct constituent is improperly connected, thereby reducing damage to sensitive parts of the instrument as well as incorrect readings.

According to certain aspects of the disclosure, the resistor or capacitance value may also serve to enable identification of the connector (and consequently the tube or other constituent attached thereto) as belonging to one of a number of classes. Such identification may enable the medical instrument to automatically operate as appropriate for the identified connector.

According to some embodiments, there is provided a tube connector including at least two conductive elements and at least one resistor electrically connected therebetween. According to some embodiments, the at least two elements are arranged such that an electrical circuit including the at least two conductive elements and the resistor will be closed when the tube connector mates with a device connector of a medical device.

According to some embodiments, a connection system of the medical device can monitor a resistor value of the at least one resistor.

According to some embodiments, the resistor value is indicative of a type of said tube connector. According to some embodiments, the resistor value is indicative of a preferred mode of operation of said tube connector.

According to some embodiments, the connection system may be configured to identify changes in the resistor value during insertion and/or revolving of the tube connector relative to the device connector.

According to some embodiments, when said resistor value is identified, the medical device is actuated. According to some embodiments, the operation mode of the medical device is based on the identified resistor value.

According to some embodiments, the at least two conductive elements may include silver, copper, gold, carbon, nickel, tin, aluminum, molybden, zinc, lithium, tungsten, brass, iron, palladium, platinum, bronze or any combination thereof.

According to some embodiments, there is provided a tube connector having at least two conductive elements and at least one capacitor electrically connected therebetween. According to some embodiments, the at least two conductive elements are arranged such that an electrical circuit will be closed when the tube connector mates with a device connector of a medical device.

According to some embodiments, a connection system of the medical device can monitor a capacitance value of the at least one capacitor. According to some embodiments, the capacitance value may be indicative of a type of the tube connector. According to some embodiments, the capacitance value is indicative of a preferred mode of operation of the tube connector.

According to some embodiments, the connection system may be configured to identify changes in the capacitance value during insertion and/or revolving of the tube connector relative to the device connector.

According to some embodiments, when the capacitance value is identified, the medical device is actuated. According to some embodiments, the operation mode of the medical device is based on the identified capacitance value.

According to some embodiments, the at least two conductive elements may include silver, copper, gold, carbon, nickel, tin, aluminum, molybdenum, zinc, lithium, tungsten, brass, iron, palladium, platinum, bronze, beryllium copper, phosphor bronze or any combination thereof.

According to some embodiments, the tube connector may include a memory chip configured to store data relating to the tube connector. According to some embodiments, the memory chip comprises an erasable programmable read only memory (EPROM) and/or an electrically erasable programmable read only memory (EEPROM).

According to some embodiments, there is provided a method including forming a tube connector; and applying at least two conductive elements and at least one resistor and/or at least one capacitor on the tube connector. According to some embodiments, the at least two conductive elements and the at least one resistor and/or the at least one capacitor may be applied such that the resistor/capacitor is electrically connected between the at least two conductive elements, such that an electrical circuit will be closed when the tube connector mates with a device connector of a medical device.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
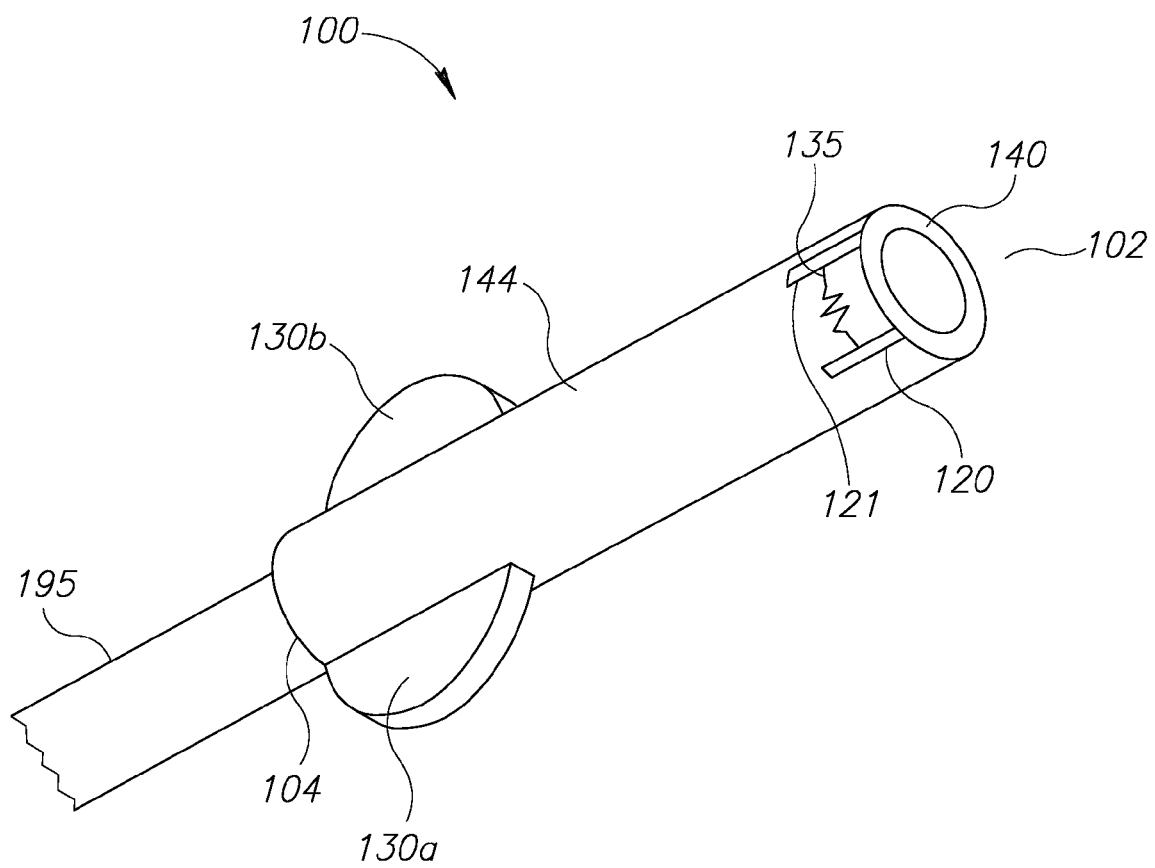
FIG. 1 schematically illustrates a perspective view of an exemplary tube connector having two conductive elements and a resistor, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a tube connector having at least two conductive elements and at least one resistor electrically connected between the at least two conductive elements. According to some embodiments, the tube connector is configured to connect to a medical device having a connection system configured to measure the resistance value of the resistor. According to some embodiments, the tube connector is configured to actuate the medical device and/or to influence the operation mode of the medical device based on the identified resistance value.

According to some embodiments, the resistor may be any one of axial lead, thick film, thin film, and SMT or combinations thereof. Each possibility is a separate embodiment. According to some embodiments, the resistance value of the resistor may be in the range of 0.0002 Ohms to 549 GOhm.

According to some embodiments, there is provided a tube connector having at least two conductive elements and at least one capacitor electrically connected between the at least two conductive elements. According to some embodiments, the tube connector is configured to connect to a medical device having a connection system configured to measure the capacitance value of the capacitor. According to some embodiments, the tube connector is configured to actuate the medical device and/or to influence the operation mode of the medical device based on the identified capacitance value.

According to some embodiments, the capacitor may be any one of an axial lead and/or an SMT. Each possibility is a separate embodiment. According to some embodiments, the capacitance value of the capacitor may include 0.01 pF to 5000 F.

As used herein, the term "tube connector" refers to a connector configured to connect between a tube, such as for example a sampling tube and a medical device (for example a gas analyzer). Alternatively or additionally, the connector can also be used for connecting any other element such as, but not limited to, cannulas, pulse oximeter probes, Electrocardiography (ECG) or Electroencephalography (EEG) electrodes, non-invasive blood pressure (NIBP) Cuffs and the like, to a medical device. The tube connector may be a radial connector, for instance a luer connector, such as a female and/or male luer connector. However other connectors, such as non-radial push-in connectors also fall under the scope of the disclosure.

As used herein, the terms "tube" unless specifically indicated otherwise, may interchangeably refer to, sample tubes, supply tubes, electrodes, probes, cables or any other suitable element configured to be connected to a medical device.

As used herein, the term "conductive element" may refer to any element capable of conducting an electric current. According to some embodiments, the conductive element may be conductive bands, conductive strips, conducting pads, conductive rings or any other suitable elements. Each possibility is a separate embodiment.

According to some embodiments, the conductive element may include a conductive material. According to some embodiments, the conductive element may be made of a conductive material. Suitable conductive materials include silver, copper, gold, carbon, nickel, tin, aluminum, molybdenum, zinc, lithium, tungsten, brass, iron, palladium, platinum, bronze, beryllium copper, phosphor bronze or any combination thereof. Each possibility is a separate embodiment.

According to some embodiments, the at least two conductive elements are arranged such that an electrical circuit including the at least two conductive elements and the at least one resistor and will be closed when the tube connector mates with a device connector of a medical device. According to some embodiments, the at least two conductive elements are arranged such that an electrical circuit including the at least two conductive elements and the at least one capacitor and will be closed when the tube connector mates with a device connector of a medical device. According to some embodiments, the device connector includes a second conductive element configured to close the electrical circuit.

According to some embodiments, the at least two conductive elements may be arranged such that that the connection system can identify a change in the resistance value during insertion of the tube connector into the device connector. Additionally or alternatively, the at least two conductive elements are arranged such that that the connection system can identify a change in the resistance value during the revolving of the tube connector relative to the device connector. According to some embodiments, the at least two conductive elements may be arranged such that that the connection system can identify a change in the capacitance value during insertion of the tube connector into the device connector. Additionally or alternatively, the at least two conductive elements are arranged such that that the connection system can identify a change in the capacitance value during the revolving of the tube connector relative to the device connector.

According to some embodiments, the at least two conductive elements may be attached to, embedded in, plated on, insert-molded in or molded on an outer wall of the tube connector. According to some embodiments, the at least two conductive elements may be attached to, embedded in or molded on an end face of the tube connector. According to some embodiments, the at least one resistor may be attached to, embedded in or molded on an outer wall of the tube connector. According to some embodiments, the at least one resistor may be attached to, embedded in or molded on an end face of the tube connector. According to some embodiments, the at least one capacitor may be attached to, embedded in or molded on an outer wall of the tube connector. According to some embodiments, the at least one capacitor may be attached to, embedded in or molded on an end face of the tube connector.

According to some embodiments, the tube connector is a primary Luer female connector having a secondary male section. According to some embodiments, the at least two conductive elements and the at least one resistor and/or capacitor may be attached to, embedded in or molded on the secondary male section of the primary Luer female connector.

According to some embodiments, the device connector is a primary Luer male connector having a secondary female section. According to some embodiments, the secondary female section includes a second conductive element configured to close an electrical circuit with the at least two conductive elements on the secondary male section of the tube connector when the primary Luer female connector and the primary Luer male connector at least partially mate with each other.

According to some embodiments, the tube connector is a primary Luer male connector having a secondary female section. According to some embodiments, the at least two conductive elements and the at least one resistor and/or capacitor may be attached to, embedded in or molded on the secondary male section of the primary Luer male connector.

According to some embodiments, the device connector is a primary Luer female connector having a secondary male section. According to some embodiments, the secondary male section includes a second conductive element configured to close an electrical circuit with the at least two conductive elements on the secondary female section of the tube connector when the primary Luer male connector and the primary Luer female connector at least partially mate with each other.

As used herein, the term "at least one" when referring to a resistor and/or a capacitor may refer to 1, 2, 3, 4, 5, or more resistors/capacitors. Each possibility is a separate embodiment. It is further understood that each resistor is electrically connected between two conductive elements. Hence, the term "at least two" when referring to conductive elements may refer to 2, 4, 6, 8, 10 or more conductive elements, each set of conductive element electrically connected to at least one resistor and/or capacitor. It is understood by one of ordinary skill in the art that each electrical circuit may include more than one resistor/capacitor (for example 2, 3 or more) electrically connected between two conductive elements.

According to some embodiment two conductive bands and a resistor/capacitor may be referred to as a set. According to one non-limiting example, the tube connector may include at least two sets of two conductive elements and a resistor/capacitor. According to some embodiments, the at least two resistors/capacitors are identical (having a same resistance/capacitance value). According to some embodiments, the at least two resistors/capacitors are different (having a different resistance/capacitance value). According to some embodiments, the at least two resistors/capacitors are arranged at a same circumferential position on the connector. According to some embodiments, the at least two sets of two conductive elements and a resistor/capacitor are arranged at different circumferential positions on the tube connector. According to some embodiments, the at least two sets of two conductive elements and a resistor/capacitor are arranged at a same longitudinal position on the connector. According to some embodiments, the at least two sets of two conductive elements and a resistor/capacitor are arranged at different longitudinal positions on the connector.

As referred to herein the term "type", "model", "class" of the connector may interchangeably be used and may relate to the interface to be used with the tube connector. According to some embodiments, the type of the connector may refer to the type of the consumable connected thereto. Non-limiting examples of types of consumables may include breath sampling tubes, oxygen delivery tubes, cannulas etc. According to some embodiment the type of the connector may refer to characteristics of the consumable connected thereto. Non-limiting examples of characteristics of the consumable include length of a tube, diameter of a tube, dead space of a tube or combinations thereof. Each possibility is a separate embodiment. According to some embodiment the type of the connector may refer to the intended use of a consumable. Non-limiting examples of intended uses include neonatal sampling tubes, sampling tubes for adults and the like.

According to some embodiment, the resistance/capacitance value measured may vary during the insertion and or revolving of the tube connector relative to the device connector. According to some embodiments, the change in the resistance/capacitance value measured during insertion of the tube connector into the device connector may be indicative of the type of the tube connector. According to some embodiments, the change in the resistance/capacitance value measured during insertion of the tube connector into the device connector may be indicative of a preferred mode of operation of the tube connector. According to some embodiments, the change in the at least one parameter during revolving of the tube connector relative to the device connector may be indicative of the type of the tube connector. According to some embodiments, the change in the at least one parameter during relative revolving of the tube connector and the device connector may be indicative of a preferred mode of operation of the tube connector.

According to some embodiments, the connector may be configured to connect to a medical device. According to some embodiments, the medical device is a capnograph.

According to some embodiments, when the resistance/capacitance value and/or the change therein is identified, the medical device may be actuated. According to some embodiments, when the resistance/capacitance value and/or the change therein is identified, the medical device may be actuated in a preferred mode of operation. According to some embodiments, when the resistance/capacitance value and/or the change therein is identified, the medical device may be deactivated.

According to some embodiments, there is provided a connection system configured to measure a resistance value of a resistor electrically connected to two conductive elements, positioned on (or otherwise attached to) a tube connector. According to some embodiments, the connection system may be configured to identify recurring changes in the resistance value during insertion of the tube connector into a device connector. Additionally or alternatively, the connection system may be configured to identify recurring changes in the resistance value during the revolving of the tube connector relative to the device connector.

According to some embodiments, there is provided a connection system configured to measure a capacitance value of a capacitor electrically connected to two conductive elements, positioned on (or otherwise attached to) a tube connector. According to some embodiments, the connection system may be configured to identify recurring changes in the capacitance value during insertion of the tube connector into a device connector. Additionally or alternatively, the connection system may be configured to identify recurring changes in the capacitance value during the revolving of the tube connector relative to the device connector.

According to some embodiments, the connection system comprises at least one detector configured to detect the resistance value of the resistor on the tube connector. According to some embodiments, the connection system comprises at least one detector configured to detect the capacitance value of the capacitor on the tube connector. According some embodiments, the at least one detector is an ohmmeter. According some embodiments, the at least one detector is a capacitance meter.

According to some embodiment, the connection system may be configured to identify the presence/absence of a connector based on the identification of the resistance/capacitance value. According to some embodiment, the connection system may be configured to identify the presence/absence of a connector based on the identification of a change in the resistance/capacitance value during insertion and/or revolving of the tube connector into the device connector.

According to some embodiments, the connection system may be further configured to identify the tube connector as having attached thereto a consumable belonging to a certain type based on the resistance/capacitance value and/or changes therein. According to some embodiments, the connection system may be further configured to distinguish between different types/classes of tube connectors. As a non-limiting example, the connection system may be configured to identify a tube connector attached to a sampling tube adapted for use with infants and to distinguish between this connector and a connector attached to a sampling tube adapted for use in adults.

According to the some embodiment, the connection system may be configured to generate at least one signal based on the resistance/capacitance value and/or changes therein. According to some embodiments, the at least one signal generated may serve as a trigger to activate a medical device. According to some embodiments, the at least one signal generated may serve as a trigger to deactivate a medical device. Alternatively or additionally, the at least one signal may serve to influence an operation mode of the medical device.

According to some embodiments, the connection system includes a device connector. According to some embodiments, the device connector includes at least one second conductive element. As used herein, the term "at least one" may refer to 1, 2, 3, 4, 5 or more second conductive element. Each possibility is a separate embodiment.

According to some embodiments the second conductive element may be a conductive strip. According to some embodiments the second conductive element may be a conductive ring. It is understood to one of ordinary skill in the art that whereas a device connector having a conductive ring will close a circuit with the at least two conducting elements when the tube connector is revolved relative to the device connector; a device connector having a conductive strip may close the circuit only at some points during the revolving of the connector. It is further understood that a conductive element positioned at a tube end (away from the inlet of the device connector) may close the electrical circuit only when the tube connector has reached a final position in the device connector or only when the tube connector is sufficiently inserted into the device connector.

Hence, according to some embodiments, connection is identified only when a tube connector reaches a final position indicating that the connector is entirely inserted into the device connector. According to some embodiments, the medical device is only actuated when the connector reaches its final position in the device connector. Additionally or alternatively, according to some embodiments, proper connection is identified when a tube connector reaches an intermediate position indicating that the tube connector is partially, but sufficiently inserted into the device connector. It is understood by one of ordinary skill in the art that sufficient connection may refer to a connection in which the tube connector is inserted adequately enough into the device connector to avoid leaks and misreadings, but does not necessarily require that the connector reaches its final connection position. According to some embodiments, the medical device is actuated when the connector reaches such intermediate and sufficient connection. In hospital and emergency environment, the number of tasks required and the limited time available, often create situations where connectors are not mated securely and firmly. Though the user is required to feel the positive feedback received when the fittings are screwed on correctly, the conditions in the medical environment often do not lend themselves for the user to be sensitive to this feedback. This may result in regions of increased diameters as well as leaks thereby negatively influencing readings of the medical device, such as but not limited to capnographic readings. On the other hand, emergency situations may require hasty connection which may be profoundly delayed if complete connection is required. Advantageously, the connector disclosed herein is configured to facilitate the connection system of the medical device to identify sufficient connection ensuring that the connector is firmly secured in the device connector and that misreadings are avoided while requiring a minimum connection time. According to some embodiments, the relative positioning of the at least two conducting element on the tube connector and of the second conductive element on the device connector may be indicative of adequate connection of the tube connector to the device connector.

According to some embodiments, the tube connector may include a memory chip configured to store data relating to the tube connector. According to some embodiments, the memory chip comprises an erasable programmable read only memory (EPROM) and/or an electrically erasable programmable read only memory (EEPROM).

As used herein "erasable programmable read only memories" and "electrically erasable programmable read only memories", may refer to a type of memory chip that retains its data when its power supply is switched off.

According to some embodiments, the memory chip may be configured to store information about the tube and/or the accessory/accessories connected to the tube. Optional information stored on the memory chip may include: presence of dehumidification tubing (e.g. Nafion), length of dehumidification tubing, presence of filter, type of filter, indicated usage, time of use, life time of the tube, tube diameter, type of respiratory device (e.g. nasal cannula) or any combination thereof. Each possibility is a separate embodiment.

According to some embodiments, there is further provided, a method for identifying a tube connector, the method comprising inserting a tube connector having at least two conductive elements and a resistor electrically connected therebetween into a device connector; and detecting a resistance value of said resistor.

According to some embodiments, there is further provided, a method for identifying a tube connector, the method comprising inserting a tube connector having at least two conductive elements and a capacitor electrically connected therebetween into a device connector; and detecting a capacitance value of said resistor.

According to some embodiments, the method includes identifying a change in the resistance/capacitance value during the insertion of the tube connector into the device connector. Additionally or alternatively, the method includes identifying a change in the resistance/capacitance value during the revolving of the tube connector relative to the device connector.

According to some embodiments, the method further includes identifying a type of said tube connector based on the resistance/capacitance value of the connector value.

According to some embodiments, the method further includes actuating a medical device, when the resistance and/or capacitance value is identified.

According to some embodiments, the method further includes producing at least one signal based on the resistance/capacitance value and/or on the identified tube connector. According to some embodiments, the at least one signal generated may serve as a trigger to activate/deactivate a medical device. Alternatively or additionally, the at least one signal may serve to influence an operation mode of the medical device.

According to some embodiments, there is further provided a method including forming a tube connector; and applying at least two conductive elements and at least one resistor electrically connected between the at least two conductive elements onto the tube connector, such that an electrical circuit will be closed when said tube connector mates with a device connector of a medical device.

According to some embodiments, there is further provided a method including forming a tube connector; and applying at least two conductive elements and at least one capacitor electrically connected between the at least two conductive elements onto the tube connector, such that an electrical circuit will be closed when the tube connector mates with a device connector of a medical device.

According to some embodiments, applying the at least two conductive elements includes attaching, molding and/or embedding the conductive elements onto the connector. According to some embodiments, applying the at least one resistor includes attaching, molding and/or embedding the resistor onto the connector. According to some embodiments, applying the at least one capacitor includes attaching, molding and/or embedding the capacitor onto the connector.

According to some embodiments, the at least at least two conductive elements may be applied on an outer wall of the tube connector. According to some embodiments, the at least at least two conductive elements may be applied on an end face of the tube connector. According to some embodiments, the at least at least one resistor may be applied on an outer wall of the tube connector. According to some embodiments, the at least at least one resistor may be applied on an end face of the tube connector. According to some embodiments, the at least at least one capacitor may be applied on an outer wall of the tube connector. According to some embodiments, the at least at least one capacitor may be applied on an end face of the tube connector.

According to some embodiments, applying the at least two conductive elements and at least one resistor and/or capacitor includes applying at least two sets of two conductive elements and at least one resistor and/or capacitor. According to some embodiments, applying the at least two sets of two conductive elements and at least one resistor and/or capacitor includes applying the at least two sets on same or different circumferential and/or longitudinal axes of the tube connector.

Reference is now made to FIG. 1, which schematically illustrates a perspective view of an exemplary tube connector, according to some embodiments.

The connector, here exemplified as connector 100, may include two ends: a tube end 104, which is the end that may be connected to a tube or any other suitable constituent; and a device end 102, which is the end that may be used to connect the connector to a device/instrument. Tube connector 100 has an elongated cylindrical-like shape; however other suitable shapes are also applicable. Tube connector 100 has two conductive strips 120 and 121 and a resistor 135, on an outer wall 144 of tube connector 100.

Tube end 104 of connector 100 includes gripping wings 130*a-b* (such gripping wings may have any shape or form and may also be absent from the connector). Device end 102 of connector 100 has an end face 140 having a circular, annular shape. Tube connector 100, is shown attached to a fluid sampling tube 195, which may be a part of a sampling line (not shown). It is understood by the skilled in the art that the sampling line may also include additional elements such as, but not limited to, a filter housing, an oral/nasal cannula and/or any other element.

According to some embodiments, tube connector 100 may be a radial connector, for instance a luer connector, such as a female and/or male luer connector (as illustrated in FIG. 1). However other connectors, such as non-radial push-in connectors also fall within the scope of the disclosure.

Figure 2:
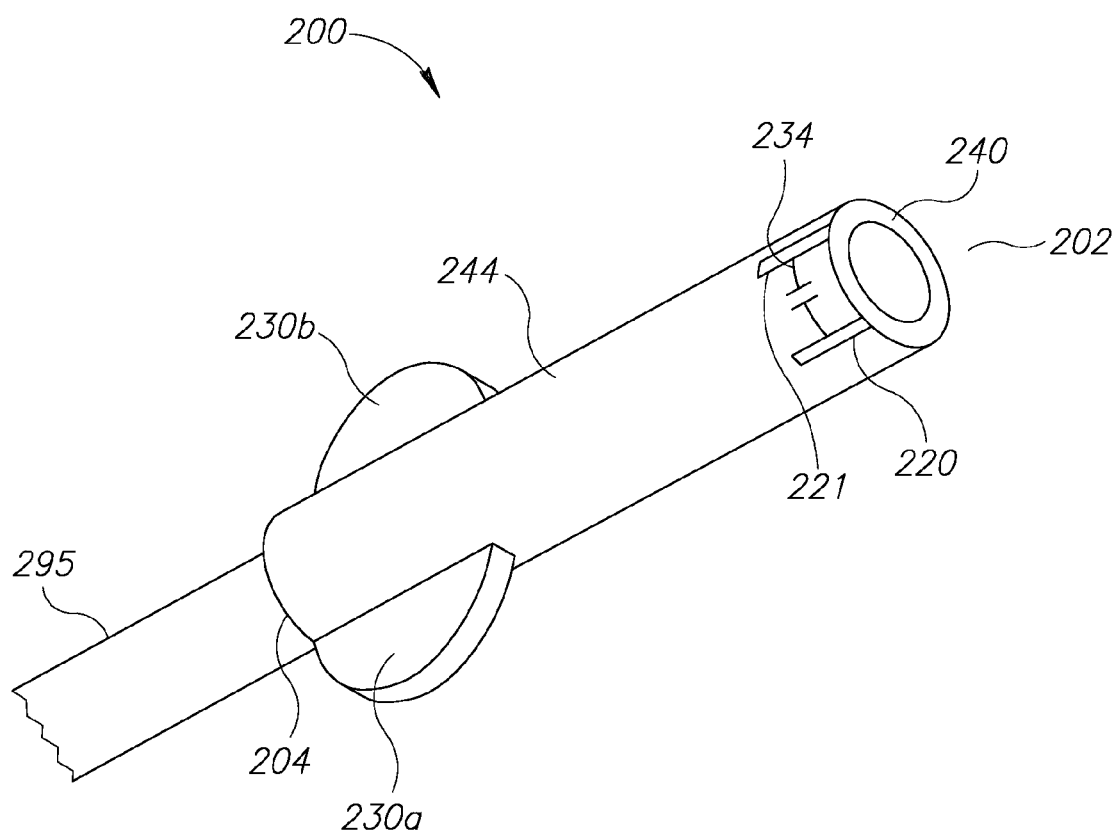
FIG. 2 schematically illustrates a perspective view of an exemplary tube connector having two conductive elements and a capacitor, according to some embodiments.
Figure 3A:
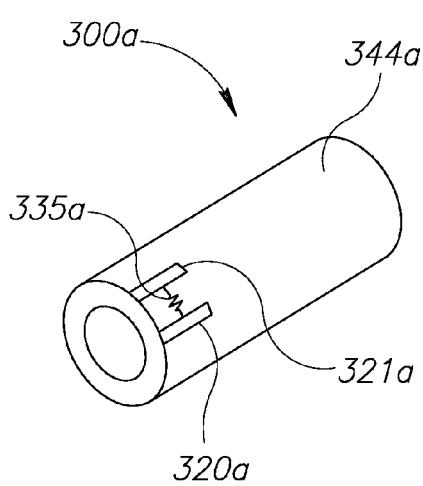
FIG. 3A schematically illustrates a perspective view of a tube connector having two conductive elements and a resistor on an outer wall thereof, according to some embodiments.
Figure 3B:
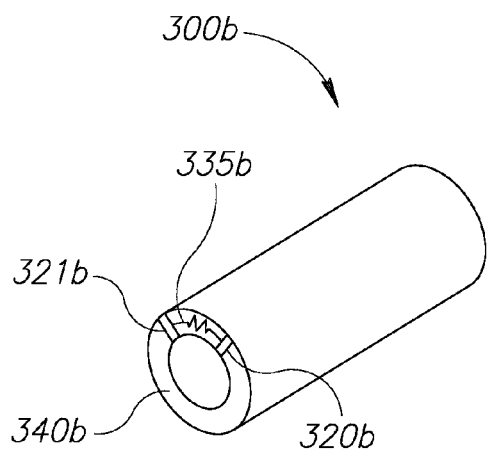
FIG. 3B schematically illustrates a perspective view of a tube connector having two conductive elements and a resistor on an end face thereof, according to some embodiments.
Figure 3C:
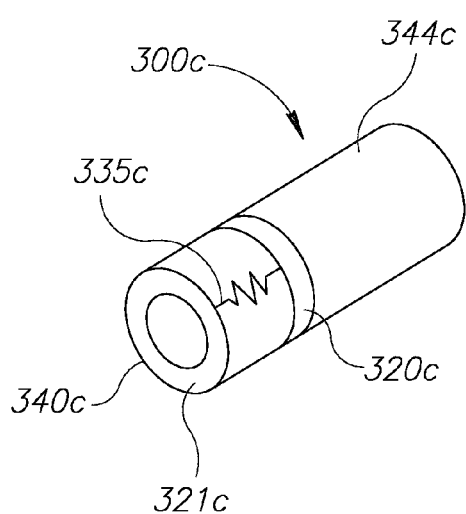
FIG. 3C schematically illustrates a perspective view of a tube connector having two conductive bands and a resistor, according to some embodiments.
Figure 3D:
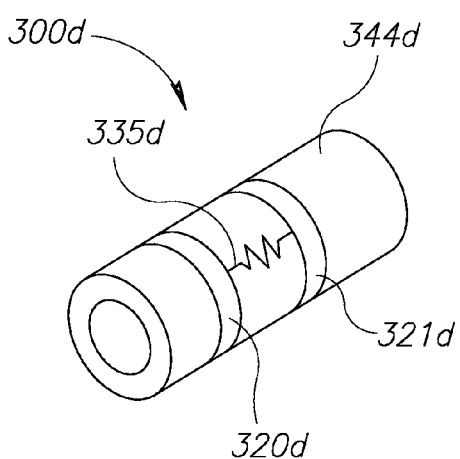
FIG. 3D schematically illustrates a perspective view of a tube connector having two conductive bands and a resistor, according to some embodiments.
Figure 3E:
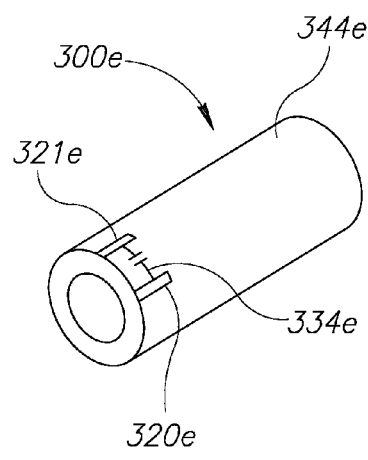
FIG. 3E schematically illustrates a perspective view of a tube connector having two conductive elements and a capacitor on an outer wall thereof, according to some embodiments.
Figure 3F:
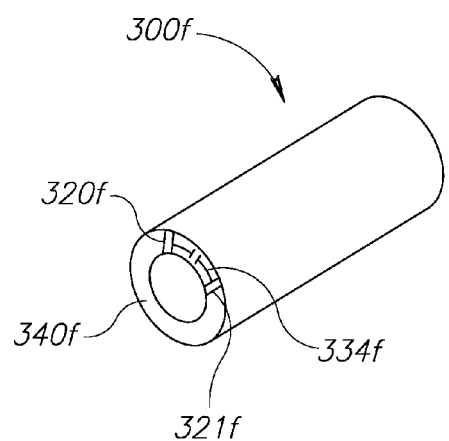
FIG. 3F schematically illustrates a perspective view of a tube connector having two conductive elements and a capacitor on an end face thereof, according to some embodiments.
Figure 3G:
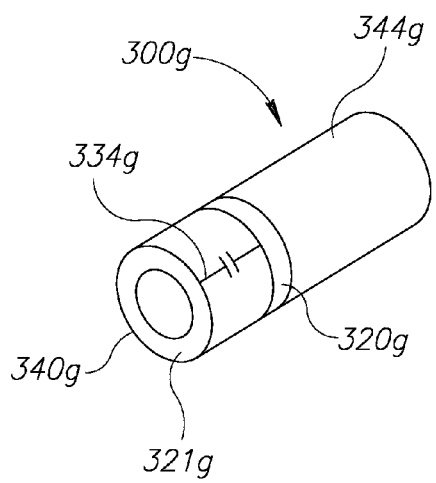
FIG. 3G schematically illustrates a perspective view of a tube connector having two conductive bands and a capacitor, according to some embodiments.
Figure 3H:
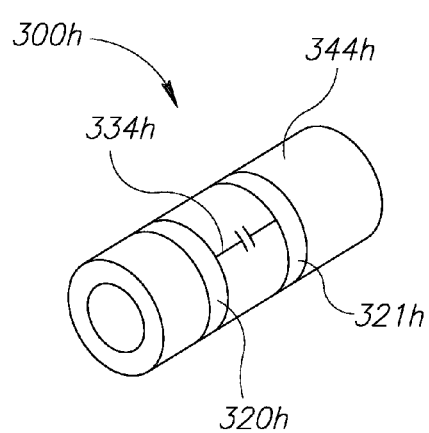
FIG. 3H schematically illustrates a perspective view of a tube connector having two conductive bands and a capacitor, according to some embodiments.

Reference is now made to FIG. 2, which schematically illustrates a perspective view of an exemplary tube connector, according to some embodiments.

The connector, here exemplified as connector 200, may include two ends: a tube end 204, which is the end that may be connected to a tube or any other suitable constituent; and a device end 202, which is the end that may be used to connect the connector to a device/instrument. Tube connector 200 has an elongated cylindrical-like shape; however other suitable shapes are also applicable. Tube connector 200 has two conductive strips 220 and 221 and a capacitor 234, on an outer wall 244 of tube connector 200.

Tube end 204 of connector 200 includes gripping wings 230a-b (such gripping wings may have any shape or form and may also be absent from the connector). Device end 202 of connector 200 has an end face 240 having a circular, annular shape. Tube connector 200, is shown attached to a fluid sampling tube 295, which may be a part of a sampling line (not shown). It is understood by the skilled in the art that the sampling line may also include additional elements such as, but not limited to, a filter housing, an oral/nasal cannula and/or any other element.

According to some embodiments, tube connector 200 may be a radial connector, for instance a luer connector, such as a female and/or male luer connector (as illustrated in FIG. 2). However other connectors, such as non-radial push-in connectors also fall within the scope of the disclosure.

Reference is now made to FIG. 3 which schematically illustrates perspective views of tube connectors comprising two conductive bands and a resistor or a capacitor. It is understood by the skilled in the art that the illustrated tube connectors are non-limiting examples and that additional configurations, not illustrated in the exemplary figures, fall within the scope of the disclosure. It is further understood that the resistance value of the resistor and its relative position on the tube connector may serve to generate an 'electric finger print' which may be utilized in identification and/or differentiation of consumables. FIG. 3A, schematically illustrates a perspective view of a tube connector 300a including two conductive strips 320a and 321a and a resistor 335a electrically connected between conductive strips 320a and 321a on an outer wall 344a of tube connector 300a. Conductive strips 320a and 321a are positioned such that an electric circuit including conductive strips 320a and 321a and resistor 335a will be closed when tube connector 300a is inserted into a device connector (not shown). FIG. 3B, schematically illustrates a perspective view of a tube connector 300b including two conductive strips 320b and 321b and a resistor 335b electrically connected between conductive strips 320b and 321b on an end face 340b of tube connector 300b. Conductive strips 320b and 321b are positioned such that an electric circuit including conductive strips 320b and 321b and resistor 335b will be closed when tube connector 300b is inserted into a device connector (not shown). FIG. 3C, schematically illustrates a perspective view of a tube connector 300c including a conductive band 320c on an outer wall 344c and a conductive band 321c on an end face 340c of tube connector 300c. Tube connector 300c does also include a resistor 335c electrically connected between conductive bands 320c and 321c. Conductive bands 320c and 321c are positioned such that an electric circuit including conductive bands 320c and 321c and resistor 335c will be closed when tube connector 300c is inserted into a device connector (not shown). FIG. 3D, schematically illustrates a perspective view of a tube connector 300d including two conductive bands 320d and 321d and a resistor 335d electrically connected between conductive bands 320d and 321d on an outer wall 344d of tube connector 300d. Conductive bands 320d and 321d are positioned such that an electric circuit including conductive bands 320d and 321d and resistor 335d will be closed when tube connector 300d is inserted into a device connector (not shown). It is understood by one of ordinary skill in the art that conductive bands formed around the circumference of the tube connector may advantageously require a less rigid alignment to make electrical contact. FIG. 3E, schematically illustrates a perspective view of a tube connector 300e including two conductive strips 320e and 321e and a capacitor 334e electrically connected between conductive strips 320e and 321e on an outer wall 344e of tube connector 300e. Conductive strips 320e and 321e are positioned such that an electric circuit including conductive strips 320e and 321e and capacitor 334e will be closed when tube connector 300e is inserted into a device connector (not shown). FIG. 3F, schematically illustrates a perspective view of a tube connector 300f including two conductive strips 320f and 321f and a capacitor 334f electrically connected between conductive strips 320f and 321f on an end face 340f of tube connector 300f. Conductive strips 320f and 321f are positioned such that an electric circuit including conductive strips 320f and 321f and capacitor 334f will be closed when tube connector 300f is inserted into a device connector (not shown). FIG. 3G schematically illustrates a perspective view of a tube connector 300g including a conductive band 320g on an outer wall 344g and a conductive band 321g on an end face 340g of tube connector 300g. Tube connector 300g also includes a capacitor 334g electrically connected between conductive bands 320g and 321g. Conductive bands 320g and 321g are positioned such that an electric circuit including conductive bands 320g and 321g and capacitor 334g will be closed when tube connector 300g is inserted into a device connector (not shown). FIG. 3H schematically illustrates a perspective view of a tube connector 300h including two conductive bands 320h and 321h and a capacitor 334h electrically connected between conductive bands 320h and 321h on an outer wall 344h of tube connector 300h. Conductive bands 320h and 321h are positioned such that an electric circuit including conductive bands 320h and 321h and capacitor 334h will be closed when tube connector 300h is inserted into a device connector (not shown). It is understood by one of ordinary skill in the art that conductive bands formed around the circumference of the tube connector may advantageously require a less rigid alignment to make electrical contact.

Figure 4A:
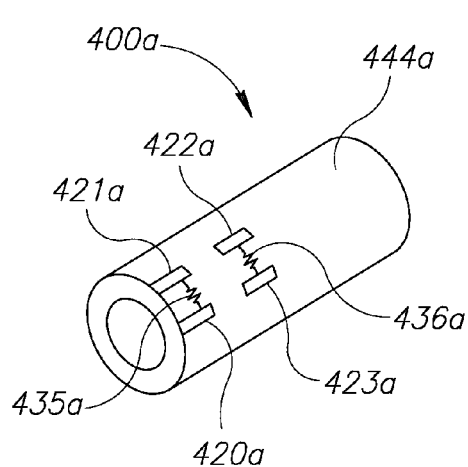
FIG. 4A schematically illustrates a perspective view of a tube connector having two sets of two conductive elements and a resistor, according to some embodiments.
Figure 4B:
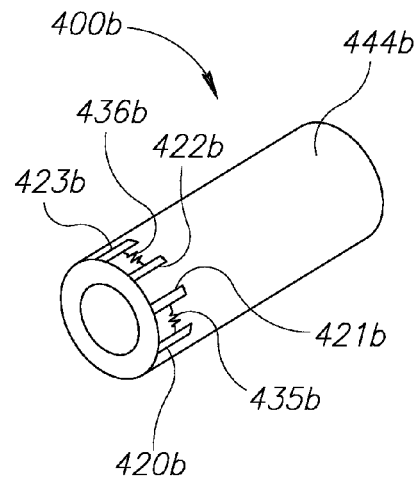
FIG. 4B schematically illustrates a perspective view of a tube connector having two sets of two conductive elements and a resistor, according to some embodiments.
Figure 4C:
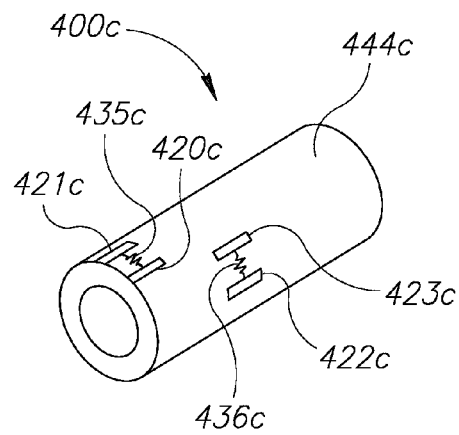
FIG. 4C schematically illustrates a perspective view of a tube connector having two sets of two conductive elements and a resistor, according to some embodiments.

Reference is now made to FIG. 4 which schematically illustrates perspective views of tube connectors comprising two sets of two conductive elements and a resistor, according to some embodiments. It is understood by one of ordinary skill in the art that one or both of the resistors may be replaced by capacitors and that such options fall within the scope of the present disclosure. It is further understood that the illustrated tube connectors are non-limiting examples and that additional configurations, not illustrated in the exemplary figures, fall within the scope of the disclosure. Moreover, the number of resistors, their resistance value and their relative position on the tube connector may serve to generate an 'electric finger print' which may be utilized in identification and/or differentiation of consumables. FIG. 4A, schematically illustrates a perspective view of a tube connector 400*a* including two electric circuits, a first electric circuit including conductive strips 420*a* and 421*a* and resistor 435*a* and a second electric circuit including conductive strips 422*a* and 423*a* and resistor 436*a* (resistors 435*a* and 436*a* having a same or a different resistance value) on an outer wall 444*a* of tube connector 400*a*. First electric circuit including conductive strips 420*a* and 421*a* and resistor 435*a*, and second electric circuit including conductive strips 422*a* and 423*a* and resistor 436*a* are positioned at similar circumferential positions, but different longitudinal positions on tube connector 400*a*. It is understood by one of ordinary skill in the art that the resistance value measured by the medical device may vary during the insertion of tube connector 400*a* into a device connector (not shown) depending on the relative position of the second conductive element on the device connector. FIG. 4B, schematically illustrates a perspective view of a tube connector 400*b* including two electric circuits, a first electric circuit including conductive strips 420*b* and 421*b* and resistor 435*b* and a second electric circuit including conductive strips 422*b* and 423*b* and resistor 436*b* (resistors 435*b* and 436*b* having a same or a different resistance value) on an outer wall 444*b* of tube connector 400*b*. First electric circuit including conductive strips 420*b* and 421*b* and resistor 435*b*, and second electric circuit including conductive strips 422*b* and 423*b* and resistor 436*b* are positioned at similar longitudinal positions, but different circumferential positions on tube connector 400*b*. It is understood by one of ordinary skill in the art that the resistance value measured by the medical device may vary during the revolving of tube connector 400*b* into a device connector (not shown) depending on the relative position of the second conductive element on the device connector. FIG. 4C, schematically illustrates a perspective view of a tube connector 400*c* including two electric circuits, a first electric circuit including conductive strips 420*c* and 421*c* and resistor 435*c* and a second electric circuit including conductive strips 422*c* and 423*c* and resistor 436*c* (resistors 435*c* and 436*c* having a same or a different resistance value) on an outer wall 444*c* of tube connector 400*c*. First electric circuit including conductive strips 420*c* and 421*c* and resistor 435*c*, and second electric circuit including conductive strips 422*c* and 423*c* and resistor 436*c* are positioned at different longitudinal and circumferential positions on tube connector 400*c*. It is understood by one of ordinary skill in the art that the resistance value measured by the medical device may vary during the revolving and/or insertion of tube connector 400*c* into a device connector (not shown) depending on the relative position of the second conductive element on the device connector.

The tube connectors in FIG. 4 all include two circuits. However as taught herein, the connectors may include more than two circuits. The configuration of the more than two circuits may be any of the configurations illustrated herein or combinations of these configurations, all possibilities fall within the scope of the disclosure.

Figure 5:
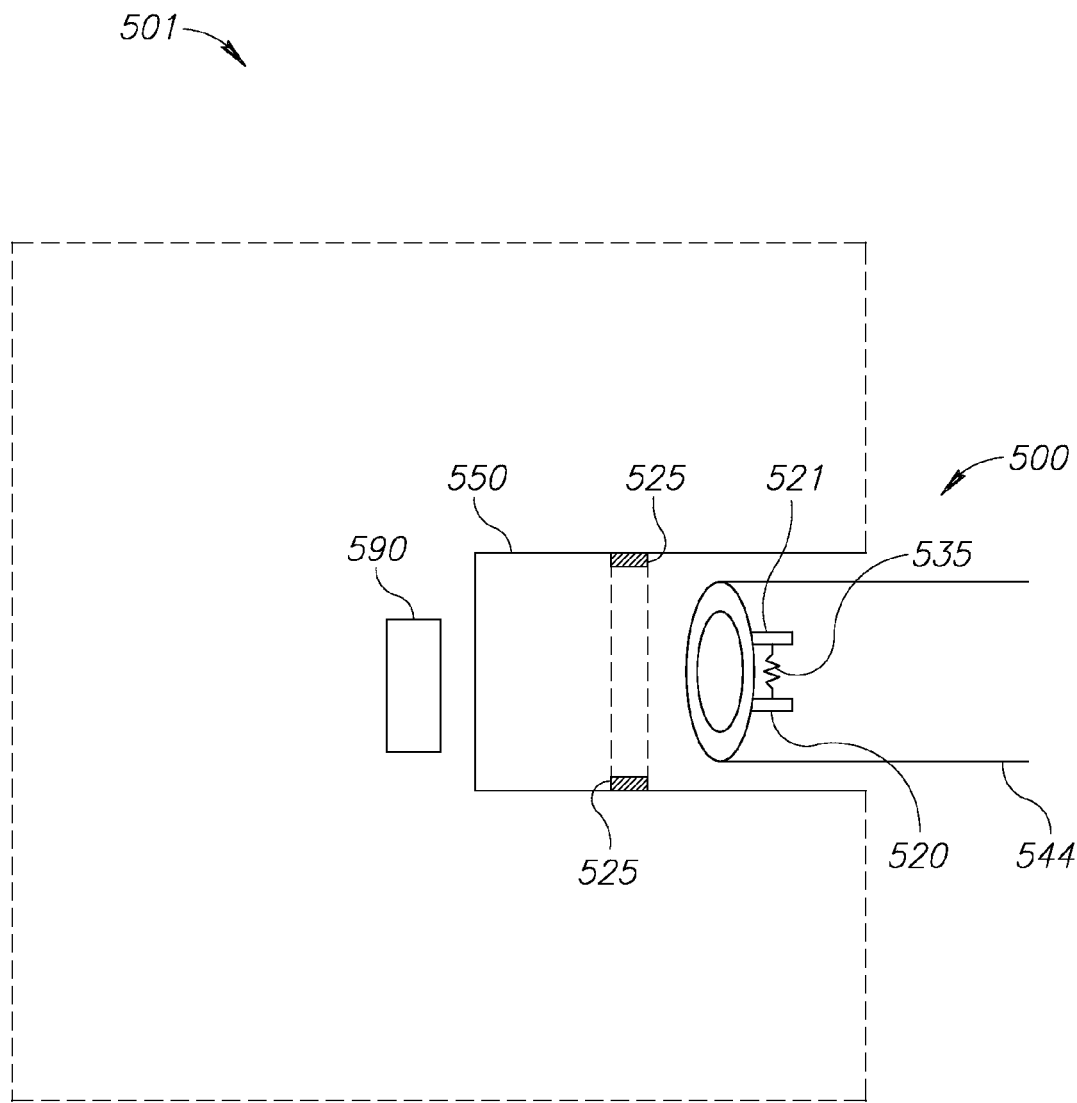
FIG. 5 schematically illustrates a perspective view of a connector having two conductive elements and a resistor and a block diagram of a connection system, according to some embodiments.

Reference is now made to FIG. 5 which schematically illustrates a perspective view of a tube connector having two conductive strips and a resistor on an outer wall thereof and a block diagram of a connection system, according to some embodiments. As essentially described hereinabove, connector 500 may include two conductive strips 520 and 521 and a resistor 535 on an outer wall 544 of tube connector 500; however connector 500 may be any of the connectors described herein. According to some embodiments, tube connector system 501 is configured to identify, authenticate, and/or specify tube connector 500. Connection system 501 includes a device connector 550 having a second conductive element 525 (here a conductive ring) configured to close an electric circuit with conductive strips 520 and 521 and supplying power thereto. Connection system 501 also includes and a detector, such as ohmmeter 590 configured to measure the resistance value of resistor 535. According to some embodiments, insertion and/or rotation of tube connector 500 into device connector 550 closes the electrical circuit including resistor 535. According to some embodiments, ohmmeter 590 is configured to detect the resistance value of resistor 535 once the electrical circuit is closed. According to some embodiments, connection system 501 may then identify proper connection of tube connector 500 to device connector 550 and optionally identify the type of the consumable attached to connector 500 based on the measured resistance value.

Figure 6:
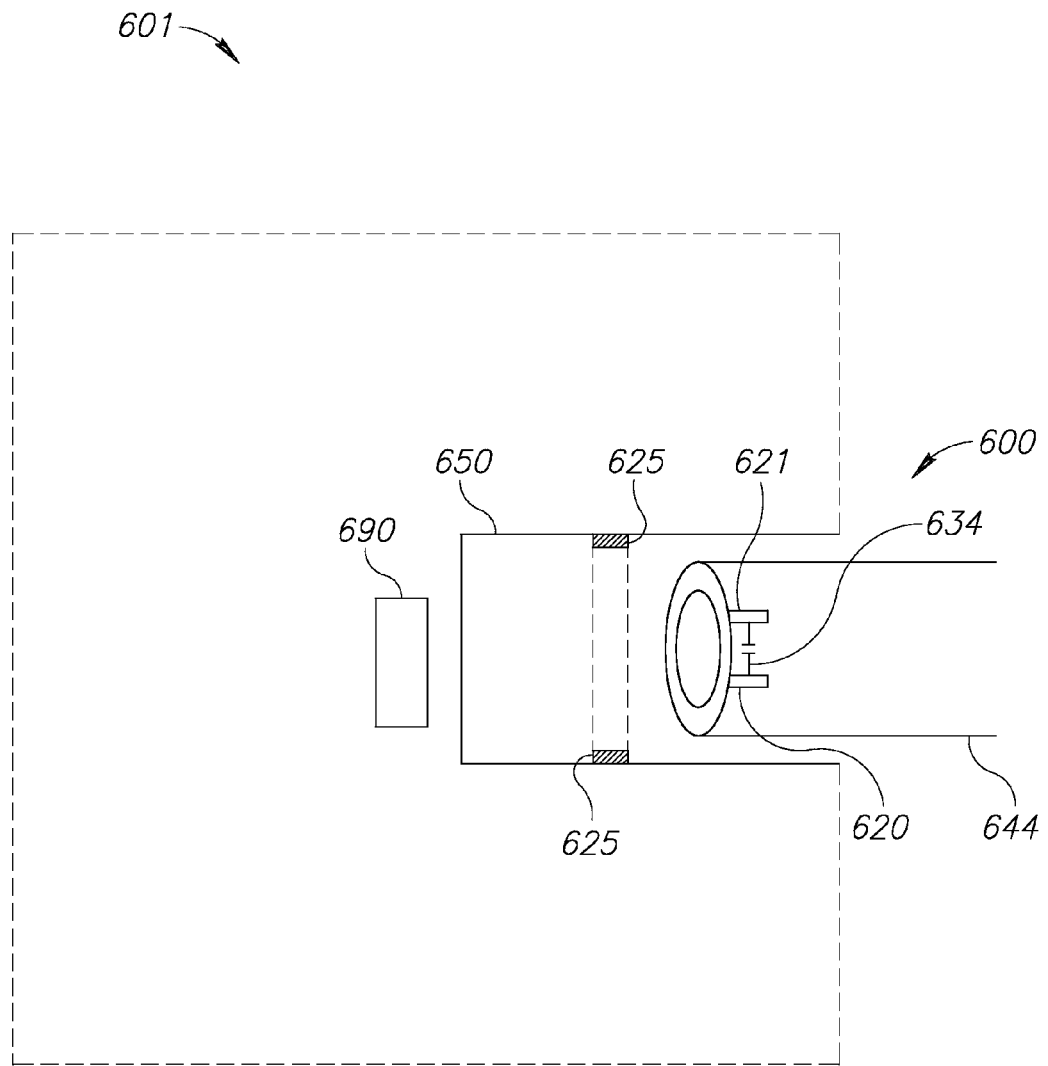
FIG. 6 schematically illustrates a perspective view of a connector having two conductive elements and a capacitor and a block diagram of a connection system, according to some embodiments.

Reference is now made to FIG. 6 which schematically illustrates a perspective view of a tube connector having two conductive strips and a resistor on an outer wall thereof and a block diagram of a connection system, according to some embodiments. As essentially described hereinabove, connector 600 may include two conductive strips 620 and 621 and a capacitor 634 on an outer wall 644 of tube connector 600; however connector 600 may be any of the connectors described herein. According to some embodiments, tube connector system 601 is configured to identify, authenticate, and/or specify tube connector 600. Connection system 601 includes a device connector 650 having a second conductive element 625 (here a conductive ring) configured to close an electric circuit with conductive strips 620 and 621 and supplying power thereto. Connection system 601 also includes a detector, such as capacitance meter 690 configured to measure the capacitance value of capacitor 634. According to some embodiments, insertion and/or rotation of tube connector 600 into device connector 650 closes an electrical circuit including capacitor 634. According to some embodiments, capacitance meter 690 is configured to detect the capacitance value of capacitor 634 once the electrical circuit is closed. According to some embodiments, connection system 601 may then identify proper connection of tube connector 600 to device connector 650 and optionally identify the type of the consumable attached to connector 600 based on the measured capacitance value.

Figure 7:
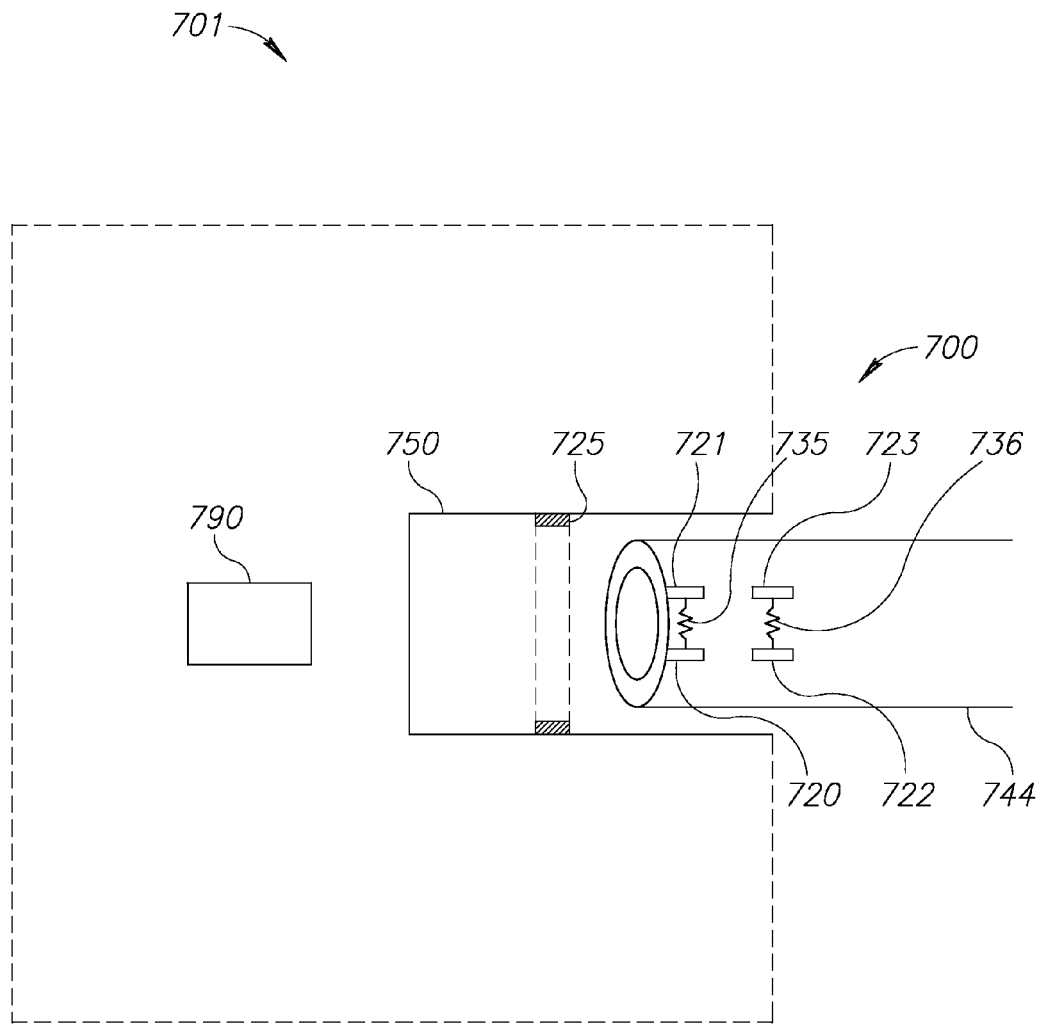
FIG. 7 schematically illustrates a perspective view of a connector having two sets of conductive elements and two resistors and a block diagram of a connection system, according to some embodiments.

Reference is now made to FIG. 7 which schematically illustrates a perspective view of a tube connector having two conductive strips and a resistor on an outer wall thereof and a block diagram of a connection system, according to some embodiments. It is understood by one of ordinary skill in the art that one or both of the resistors may be replaced by capacitors and that such options fall within the scope of the present disclosure. It is further understood that the illustrated tube connectors are non-limiting examples and that additional configurations, not illustrated in the exemplary figures, fall within the scope of the disclosure. Moreover, the number of resistors, their resistance value and their relative position on the tube connector may serve to generate an 'electric finger print' which may be utilized in identification and/or differentiation of consumables.

As essentially described hereinabove, connector 700 may include a first set of two conductive strips 720 and 721 and a resistor 735 and a second set of two conductive strips 722 and 723 and a resistor 736 on an outer wall 744 of tube connector 700; however connector 700 may be any of the connectors described herein. According to some embodiments, tube connector system 701 is configured to identify, authenticate, and/or specify tube connector 700. Connection system 701 includes a device connector 750 having a second conductive element 725 (here a conductive ring) configured to close an electric circuit with conductive strips 720 and 721 or conductive strips 722 and 723 and supplying power thereto. Connection system 701 also includes a detector, such as ohmmeter 790 configured to measure the resistance value of each of the resistors 735 or 736. According to some embodiments, insertion and/or rotation of tube connector 700 into device connector 750 first closes an electrical circuit including resistor 735 and upon further insertion/revolving including resistor 736. According to some embodiments, ohmmeter 790 is configured to sequentially detect the resistance value of each of the resistors 735 and 736 during insertion and/or revolving of tube connector 700 into device connector 750. According to some embodiments, connection system 701 may identify proper connection of tube connector 700 to device connector 750 when the second resistance value is measured. Alternatively, proper connection is identified when a change in resistance is measured. Optionally, connection system 701 is configured to identify the type of the consumable attached to connector 700 based on the sequentially measured resistance values.

Figure 8:
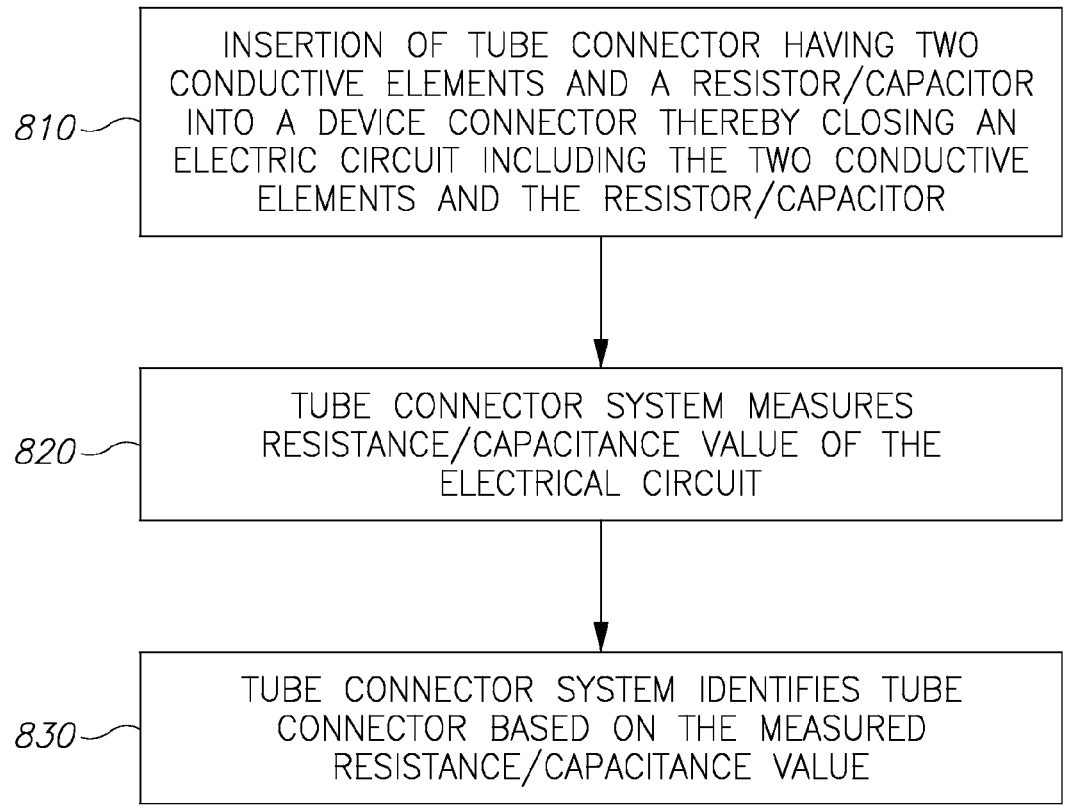
FIG. 8 is an illustrative flowchart of identification of a tube connector, according to some embodiments.

Reference is now made to FIG. 8 which is an illustrative flowchart of identification of a tube connector, according to some embodiments. In step 810, a tube connector having two conductive strips and a resistor and/or a capacitor (such as for example, but not limited to, tube connectors 100 and 200, described above) is inserted into a device connector, thereby closing an electric circuit including the two conductive strips and the resistor and/or capacitor. In step 820 the resistance and/or capacitance value is measured by detectors of a tube connector system. In step 830, the tube connector is identified based on the measured resistance and/or capacitance value.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What is claimed is:

1. A tube connector comprising at least two conductive elements and at least one resistor electrically connected therebetween, said at least two elements arranged such that an electrical circuit comprising said at least two conductive elements and said resistor will be closed when said tube connector mates with a device connector of a medical device;

wherein a connection system of said medical device can monitor a resistor value of said at least one resistor;

wherein said connection system is further configured to identify changes in said resistor value during insertion and/or revolving of said tube connector relative to said device connector;

wherein a memory chip configured to store data relating to the tube connector.

2. The tube connector of claim 1, wherein said resistor value is indicative of a type of said tube connector.

3. The tube connector of claim 1, wherein said resistor value is indicative of a referred mode of operation of said tube connector.

4. The tube connector of claim 1, wherein when said resistor value is identified, said medical device is actuated.

5. The tube connector of claim 1, wherein an operation mode of said medical device is based on said identified resistor value.

6. The tube connector of claim 1, wherein said at least two conductive elements comprise silver, copper, gold, carbon, nickel, tin, aluminum, molybdenum, zinc, lithium, tungsten, brass, iron, palladium, platinum, bronze beryllium copper, phosphor bronze or any combination thereof.

7. The tube connector of claim 1, wherein said memory chip comprises an erasable programmable read only memory (EPROM) and/or an electrically erasable programmable read only memory (EEPROM).

8. A tube connector comprising at least two conductive elements and at least one capacitor electrically connected therebetween, said at least two conductive elements arranged such that an electrical circuit will be closed when said tube connector mates with a device connector of a medical device;

wherein a connection system of said medical device can monitor a capacitance value of said at least one capacitor;

wherein said connection system is further configured to identify changes in said capacitance value during insertion and/or revolving of said tube connector relative to said device connector;

wherein said memory chip comprises an erasable programmable read only memory (EPROM) and/or an electrically erasable programmable read only memory (EEPROM).

9. The tube connector of claim 8, wherein said capacitance value is indicative of a type of said tube connector.

10. The tube connector of claim 8, wherein said capacitance value is indicative of a preferred mode of operation of said tube connector.

11. The tube connector of claim 8, wherein when said capacitance value is identified, said medical device is actuated.

12. The tube connector of claim 8, wherein an operation mode of said medical device is based on said identified capacitance value.

13. The tube connector of claim 8, wherein the at least two conductive elements comprise silver, copper, gold, carbon, nickel, tin, aluminum, molybdenum, zinc, lithium, tungsten, brass, iron, palladium, platinum, bronze, beryllium copper, phosphor bronze or any combination thereof.

14. The tube connector of claim 8, further comprising a memory chip configured to store data relating to the tube connector.

* * * * *